United States Patent
Bombardelli

(10) Patent No.: US 7,976,881 B2
(45) Date of Patent: Jul. 12, 2011

(54) COMBINATIONS OF VASOACTIVE AGENTS, THEIR USE IN THE PHARMACEUTICAL AND COSMETIC FIELD, AND FORMULATIONS CONTAINING THEM

(75) Inventor: Ezio Bombardelli, Groppello Cairoli (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 10/563,965

(22) PCT Filed: Jul. 6, 2004

(86) PCT No.: PCT/EP2004/007375
§ 371 (c)(1),
(2), (4) Date: Jun. 20, 2006

(87) PCT Pub. No.: WO2005/004858
PCT Pub. Date: Jan. 20, 2005

(65) Prior Publication Data
US 2007/0020349 A1    Jan. 25, 2007

(30) Foreign Application Priority Data
Jul. 11, 2003  (IT) .............................. MI2003A1427

(51) Int. Cl.
*A61K 36/16* (2006.01)
*A61K 36/00* (2006.01)

(52) U.S. Cl. ........................................ 424/752; 424/725
(58) Field of Classification Search .................. None
See application file for complete search history.

(56) References Cited

U.S. PATENT DOCUMENTS

| | | | |
|---|---|---|---|
| 5,176,919 A * | 1/1993 | Bertini Curri et al. | 424/450 |
| 5,523,090 A * | 6/1996 | Znaiden et al. | 424/401 |
| 5,529,769 A * | 6/1996 | Cho et al. | 424/74 |
| 5,665,335 A * | 9/1997 | Bombardelli et al. | 424/70.1 |
| 5,679,358 A * | 10/1997 | Bombardelli et al. | 424/401 |
| 6,267,996 B1 * | 7/2001 | Bombardelli et al. | 424/773 |
| 6,409,996 B1 * | 6/2002 | Plaschke | 424/59 |
| 2003/0069618 A1 * | 4/2003 | Smith et al. | 607/100 |

FOREIGN PATENT DOCUMENTS

| | | |
|---|---|---|
| EP | 0 418 806 | 3/1991 |
| EP | 0 680 761 | 11/1995 |
| EP | 0 692 250 | 1/1996 |
| FR | 2 740 681 | 5/1997 |
| WO | WO 01/78674 | 10/2001 |
| WO | WO 02/098436 | * 12/2002 |
| WO | WO 02/098436 A1 | * 12/2002 |

OTHER PUBLICATIONS

Thiolon et al., An in vitro, ex vivo, and in vivo demonstration of the lipolytic effect of slimming liposomes: an unexpected alpha-2-adrenergic antagonism, J. Cosmet. Sci., 53: 209-218, 2002.*
Phlebologie, vol. 23, No. 3, 1994, pp. 71-77, XP009039687 p. 72, middle col., paragraph 2 p. 74, right-hand col., paragraph 1- p. 76, middle col., paragraph 1.
Rossi A B R et al: "Cellulite: A Review" JEADV. Journal of the European Academy of Dermatology and Venereology, Elsevier Science Publishers, Amsterdam, NL, vol. 14, No. 4, 2000, pp. 251-262, XP009011440 ISSN: 0926-9959 p. 251, left-hand col., paragraph 2 p. 258, right-hand col., paragraph 3—p. 259, left-hand col., paragraph 2.
Bombardelli F et al: "*Aesculus Hippocastanum* L" Fitoterapia, IDB Holding, Milan, IT, vol. 67, No. 6, 1996, pp. 483-511, XP000917088 ISSN: 0367-326X p. 496, paragraph 5, p. 500, paragraph 3-5, p. 505, paragraph 4—p. 508, paragraph 5.

\* cited by examiner

*Primary Examiner* — Qiuwen Mi
(74) *Attorney, Agent, or Firm* — Young & Thompson

(57) ABSTRACT

Combinations of vasoactive substances which act at venous or arterial level with phosphodiesterase inhibitors including phosphodiesterase V, in particular: visnadin or esculoside; at least one compound selected from icarin or derivatives thereof or extracts containing it, *Gingko biloba* dimeric flavones either in the free form or complexed with phospholipids, amentoflavone; at least one compound selected from escin, escin beta-sitosterol complexed with phospholipids, sericoside, sericoside complexed with phospholipids or *Centella asiatica* extract in the free form or complexed with phospholipids. The formulations are useful in reducing parmiculopathy and problems associated with venous insufficiency of the lower limbs.

3 Claims, No Drawings

COMBINATIONS OF VASOACTIVE AGENTS, THEIR USE IN THE PHARMACEUTICAL AND COSMETIC FIELD, AND FORMULATIONS CONTAINING THEM

This application is a National Stage Application of PCT/EP2004/007375, filed Jul. 6, 2004, which claims priority to Italian Application MI 2003A001427, filed Jul. 11, 2003.

FIELD OF INVENTION

This invention relates to combinations of vasoactive substances which act at venous or arterial level with phosphodiesterase inhibitors, including cGMP phosphodiesterase V.

BACKGROUND TO THE INVENTION

Visnadine is a coumarin mainly found in the seeds of *Ammi visnaga*, a plant traditionally used to treat anginoid disorders. The compound has been used in the pharmaceutical field as a coronary dilator.

It has also been demonstrated that this compound, when applied topically, has a strong vasokinetic action on the precapillary arteries and arterioles, and increases blood flow and tissue perfusion (EP 0418806). The supply of blood to the tissue involves better nutrition and the elimination of metabolic waste, with consequent benefits for the treated area. Visnadine also has an anti-phosphodiesterase activity.

Esculoside, a coumarin glucoside present in many plants, such as *Aesculus hippocastanuin, Fraxinus communis* etc., possesses a vasokinetic action and venotropic activity at both venous and arterial levels.

Icarin and derivatives thereof, which possess activity on cGMP phosphodiesterase V, are useful activators of the microcirculation in certain areas.

Amentoflavone is a biflavone present in modest amounts in numerous plants, such as *Gingko biloba, Brakeringea zanguebarica* and *Taxus* sp.

The saponins of horse chestnut or *Centella asiatica* act on the venous and lymphatic system, where they perform an anti-oedematous action that facilitates lymph drainage.

DESCRIPTION OF THE INVENTION

The invention relates to pharmaceutical, dietetic, cosmetic or nutraceutical compositions comprising:
- visnadine or esculoside;
- at least one compound selected from icarin or derivatives thereof or extracts containing it, *Gingko biloba* dimeric flavones in the free form or complexed with phospholipids, and amentoflavone;
- at least one compound selected from escin, escin beta-sitosterol complexed with phospholipids, sericoside, sericoside complexed with phospholipids or *Centella asiatica* extract in the free form or complexed with phospholipids.

The combination of vasoactive substances according to the invention, which act simultaneously at arterial and venous level and on lymph drainage, reduces stasis oedema, which is one of the first symptoms of chronic venous insufficiency, with pathological consequences ranging from cellulitis to crural ulcers of various aetiologies. The warning signs of circulatory deficiency of the lower limbs include below-normal skin temperature, a feeling of heaviness in the legs, and acroasphyxial syndromes with peripheral pain. Various attempts have been made to treat these symptoms, but with modest success.

It has now surprisingly been found that the formulations according to the invention, containing compounds with different action mechanisms, prevent peripheral vascular and tissue degeneration.

The most common case is cellulitis or degenerative panniculopathy. Before the formation of painful fibrous nodules or fat deposits due to degeneration of the adipocytes, cellulitis is caused by seepage of fluids and protein into the perivascular spaces as a result of venous insufficiency. The resulting oedema, due to mechanical compression, reduces the free circulation of the arterial bloodstream. Under these circumstances the adipocytes accumulate fats, become enlarged and take away space from other cells. Treatment with anti-cellulitis formulations should begin at this point if the maximum success is to be achieved. The association according to the invention enables the condition to be treated at the pre-pathological stage, in order to prevent it from progressing to peripheral damage. The same formulations can also be used successfully even when the disorder has become chronic, to eliminate painful sensations and reduce unwanted adipose masses with long-term treatments, by means of lipase stimulation induced by the persistence of cyclical nucleotides in the tissues.

Icarin derivatives which can be used according to the invention as an alternative to icarin include 7-hydroxyethyl-icarin, 7-ethylamino-icarin, 7-aminoethyl-icarin, 7-hydroxyethyl-3-0-ramnosyl-icarin, 7-aminoethyl-3-ramnosyl-icarin, 8-dihydro-icarin and its glucosides in 7 and 3, and 7-hydroxyethyl-7-desgluco-icarin.

The compositions according to the invention preferably contain visnadine.

The compositions according to the invention typically have the following concentration ranges by weight:
- visnadine or esculoside: 0.05-2%;
- amentoflavone or *Gingko biloba* dimers in the free form or complexed with phospholipids: 0.1-1%;
- icarin or derivatives thereof or extracts containing it: 0.1-1%;
- at least one compound selected from among escin, escin beta-sitosterol complexed with phospholipids, sericoside, sericoside complexed with phospholipids or *Centella asiatica* extract, in the free form or complexed with phospholipids: 0.5%-2%.

These compounds can be incorporated in the most common pharmaceutical and cosmetic formulations, such as oil-in-water and water-in-oil emulsions, suitably carried by excipients, surfactants and solubilisers.

Moreover, products can be formulated in cream, milk and gel form for treatment of large areas of the skin.

The following examples illustrate the invention in detail.

EXAMPLE 1

| Gel formulation | |
|---|---|
| Visnadin | 0.25 g |
| 7-hydroxyethyl-7-desgluco-icarin | 0.35 g |
| Amentoflavone | 0.25 g |
| Escin | 1.00 g |
| Lecithin | 20.00 g |
| Cholesterol | 0.50 g |
| Ethanol | 8.00 g |
| Butylhydroxy toluene | 0.01 g |
| Imidazoline urea | 0.30 g |
| Hydroxypropyl-methylcellulose | 2.00 g |
| Water | qs to 100 g |

EXAMPLE 2

| Gel formulation | |
| --- | --- |
| Esculoside | 1.00 g |
| Icarin | 0.35 g |
| Amentoflavone | 0.25 g |
| Escin | 1.00 g |
| Lecithin | 20.00 g |
| Cholesterol | 0.50 g |
| Ethanol | 8.00 g |
| Butylhydroxy toluene | 0.01 g |
| Imidazoline urea | 0.30 g |
| Hydroxypropyl-methylcellulose | 2.00 g |
| Water | qs to 100 g |

EXAMPLE 3

| gel formulation | |
| --- | --- |
| Visnadin | 0.25 g |
| 7-Hydroxyethyl-7-desgluco-icaritin | 0.35 g |
| Gingko biloba dimers complexed with phospholipids | 0.25 g |
| Escin beta-sitosterol complexed with phospholipids | 1.00 g |
| Lecithin | 20.00 g |
| Cholesterol | 0.50 g |
| Ethanol | 8.00 g |
| Butylhydroxy toluene | 0.01 g |
| Imidazoline urea | 0.30 g |
| Hydroxypropyl-methylcellulose | 2.00 g |
| Water | qs to 100 g |

EXAMPLE 4

| Gel formulation | |
| --- | --- |
| Esculoside | 0.25 g |
| 7-Hydroxyethyl-7-desgluco-icaritin | 0.35 g |
| Amentoflavone | 0.25 g |
| Sericoside | 1.00 g |
| Lecithin | 20.00 g |
| Cholesterol | 0.50 g |
| Ethanol | 8.00 g |
| Butylhydroxy toluene | 0.01 g |
| Imidazoline urea | 0.30 g |
| Hydroxypropyl-methylcellulose | 2.00 g |
| Water | qs to 100 g |

EXAMPLE 5

| Gel formulation | |
| --- | --- |
| Visnadin | 0.3 g |
| Amentoflavone | 0.4 g |
| Centella asiatica extract | 1.0 g |
| Lecithin | 20.00 g |
| Cholesterol | 0.50 g |
| Ethanol | 8.00 g |
| Butylhydroxy toluene | 0.01 g |
| Imidazoline urea | 0.30 g |
| Hydroxypropyl-methylcellulose | 2.00 g |
| Water | qb 100 g |

The invention claimed is:

1. A pharmaceutical, cosmetic, dietetic or nutraceutical composition comprising:
    a combination of vasoactive agents consisting of a first vasoactive agent, a second vasoactive agent, and a third vasoactive agent,
    the first vasoactive agent being 0.05-2% by weight of the composition,
    the second vasoactive agent being 0.1-1% by weight of the composition, and
    the third vasoactive agent being 0.5-2% by weight of the composition,
wherein,
    the first vasoactive agent is visnadin or esculoside,
    the second vasoactive agent is *Ginkgo biloba* dimeric flavones, either in a free form or complexed with phospholipids, or amentoflavone, and
    the third vasoactive agent is a compound selected from the group consisting of escin, escin beta-sitosterol complexed with phospholipids, and *Centella asiatica* extract in a free form or complexed with phospholipids.

2. The composition as claimed in claim 1, wherein the combination of vasoactive agents is incorporated into a composition is in a form selected from the group consisting of a cream, a gel, a lotion, and a milk.

3. The composition as claimed in claim 1, wherein,
    the first vasoactive agent is Visnadin,
    the second vasoactive agent is *Ginkgo biloba* dimers complexed with phospholipids, and
    the third vasoactive agent is escin beta-sitosterol complexed with phospholipids.

* * * * *